United States Patent [19]

Plomp

[11] 4,261,183

[45] Apr. 14, 1981

[54] COOLING DEVICE

[75] Inventor: Ridderus W. Plomp, AX Zoetermeer, Netherlands

[73] Assignee: Gist-Brocades N.V., Delft, Netherlands

[21] Appl. No.: 81,914

[22] Filed: Oct. 4, 1979

[30] Foreign Application Priority Data

Oct. 6, 1978 [NL] Netherlands ......................... 7810089

[51] Int. Cl.³ .............................................. F25D 25/02
[52] U.S. Cl. ...................................... 62/381; 62/383; 62/63; 198/952
[58] Field of Search ................... 62/63, 381, 378, 383; 198/778, DIG. 952

[56] References Cited

U.S. PATENT DOCUMENTS

| 3,638,451 | 2/1972 | Brandt | 62/381 |
| 3,952,541 | 4/1976 | Rigoli | 62/381 |

Primary Examiner—Ronald C. Capossela
Attorney, Agent, or Firm—Fleit & Jacobson

[57] ABSTRACT

A device for solidifying a layer of a liquid that solidifies upon cooling, such as agar, the liquid being contained in a row of petri-dishes or the like. The device utilizes a horizontally rotatable disc for receiving the dishes, a mechanism for supplying dishes to the disc, and a mechanism for removing the dishes, with solidified liquid, from the disc. A cooling mechanism is positioned below the disc to cool the disc and thereby cool the dishes. A mechanism is provided for slowly rotating the disc so that surfaces of materials in the dishes solidify in a non-rippled manner.

11 Claims, 2 Drawing Figures

COOLING DEVICE

BACKGROUND OF THE INVENTION

1. Field of the Invention

The invention relates to a device for solidifying a layer of a liquid that solidifies upon cooling, such as agar contained in a row of petri-dishes or the like. The invention particularly relates to a device which may be combined with existing apparatuses for the preparation of agar plates in petri-dishes.

2. Description of the Prior Art

Modern apparatuses enable the manufacture of agar plates in petri-dishes in large numbers, so that a laboratory worker may quickly have large numbers thereof at his disposal for testing large series of microbiological activities and other purposes. Dishes are filled automatically with a predetermined amount of liquid agar. The dishes are supplied to a stacker until a predetermined height is reached. Those stacks may then be taken from the apparatus for further use. In this automatic process, when the dishes leave the supplier, the agar contained therein is still in a liquid state. Thus, the dishes are stacked while the agar is liquid, so that the agar solidifies in stacked condition. Since the dishes are steadily in motion during stacking, i.e., during solidifying, a rippled surface is caused. It is evident that this rippled surfface is not desired, since it influences in general, inadmissibly disadvantageously the accuracy of biological activity measurements to be made afterwards.

The above mentioned disadvantage could be avoided by placing, between the supplier and the stacker, a cooling zone, in order that the petri dishes reach the stacker when the agar is solidified. To achieve such purpose, a relatively long cooling zone would be necessary, resulting in much occupied room.

SUMMARY OF THE INVENTION

It is an object of the invention to provide a device in which agar in petri-dishes is allowed sufficient time to solidify, but which occupies only little room. As a result, the present invention provides a device for producing agar plates with smooth surfaces.

According to the invention, there is provided a device for solidifying a layer of a liquid solidifying upon cooling, such as agar contained in a row of petri-dishes or the like, characterized in that the device comprises a horizontally rotatable disc of a heat-conducting material, onto which the petri-dishes or the like may be pushed, means to remove the petri-dishes with solidified liquid from the disc, a cooling means below the disc to cool the disc, and means allowing the surface of the liquid to solidify in a non-rippled manner.

By the use of a disc whereupon the petri-dishes may be conveyed, during which transport the liquid, generally agar, is allowed to solidify, the invention provides a compact cooling device easily realizing agar plates with smooth, non-rippled surfaces. Obtaining of a smooth, non-rippled surface may be realized by giving the disc a large moment of inertia, e.g., by applying a disc having a certain weight, or a disc provided with an outer ring of increased weight. A rippled surface is further avoided by flexibly driving the disc, e.g., by means of an elastic material, such as rubber. Foreign oscillations, e.g., caused by starting and stopping the driving motor, may thus be avoided to a large extent. Allowing a little slip when stopping and starting the motor also promotes the formation of a smooth surface of the agar plates. Obtaining a smooth surface of the agar plates is further facilitated by the use of a driving motor with a slow start and stop. The location of the driving motor at the periphery of the disc or, if the disc is provided with a protection hood, at the periphery of that hood, further promotes the smooth surface. Additionally, cooling of the lower side of the petri-dishes promotes a smooth surface. In this way, condensation on the cover, which could form drops falling onto the agar surface, is avoided. Such condensation could happen if the cover is colder than the agar. Moreover, avoiding condensation is important for forming a sufficiently homogeneous agar plate, having an upper surface without locally lower agar concentrations, which concentrations would allow diffusion from one inoculation location to another after inoculating the plates.

The device according to the invention may be placed between the supplier and the stacker without much ado. The supplier pushes the petri-dishes with still liquid agar onto the disc of the device according to the invention. During transport on the disc, the petri-dishes are cooled, allowing the agar to become solid. The above mentioned measures avoid agar plates with a rippled surface. After solidification of the agar, the petri-dishes are removed from the disc to continue their way to the stacker to be stacked. The disc may be rotated intermittently, so that each petri-dish or the like to be cooled may be pushed onto the disc while standing still. It is also possible to push the petri-dishes onto a continuously rotating disc. The speed of rotation of the disc is preferably regulated by the amount of liquid to be dosed into the petri-dishes, so that the effective cooling time is adapted to the amount of agar to be cooled.

The cooling device according to the invention may also be used in cases where the agar-plates are prepared by hand and, after passing the cooling device, are taken away by hand. Also, in that case, an important saving of room is obtained, since cooling and solidifying of the agar plates occupies only little room.

It is evident that the lower side of the disc may be rough and/or may be provided with a number of concentric cooling ribs, with the cooling means therebetween in order to obtain a cooling as efficient as possible.

The invention, and its objects and advantages, will become more apparent in the detailed description of a preferred embodiment hereinafter presented.

BRIEF DESCRIPTION OF THE DRAWING

The invention is further illustrated by a drawing in which.

DESCRIPTION OF THE PREFERRED EMBODIMENT

The present description will be directed in particular to elements forming part of, or cooperating more directly with, the present invention. Elements not specifically shown or described herein are understood to be selectable from those known in the art.

Figure 1:
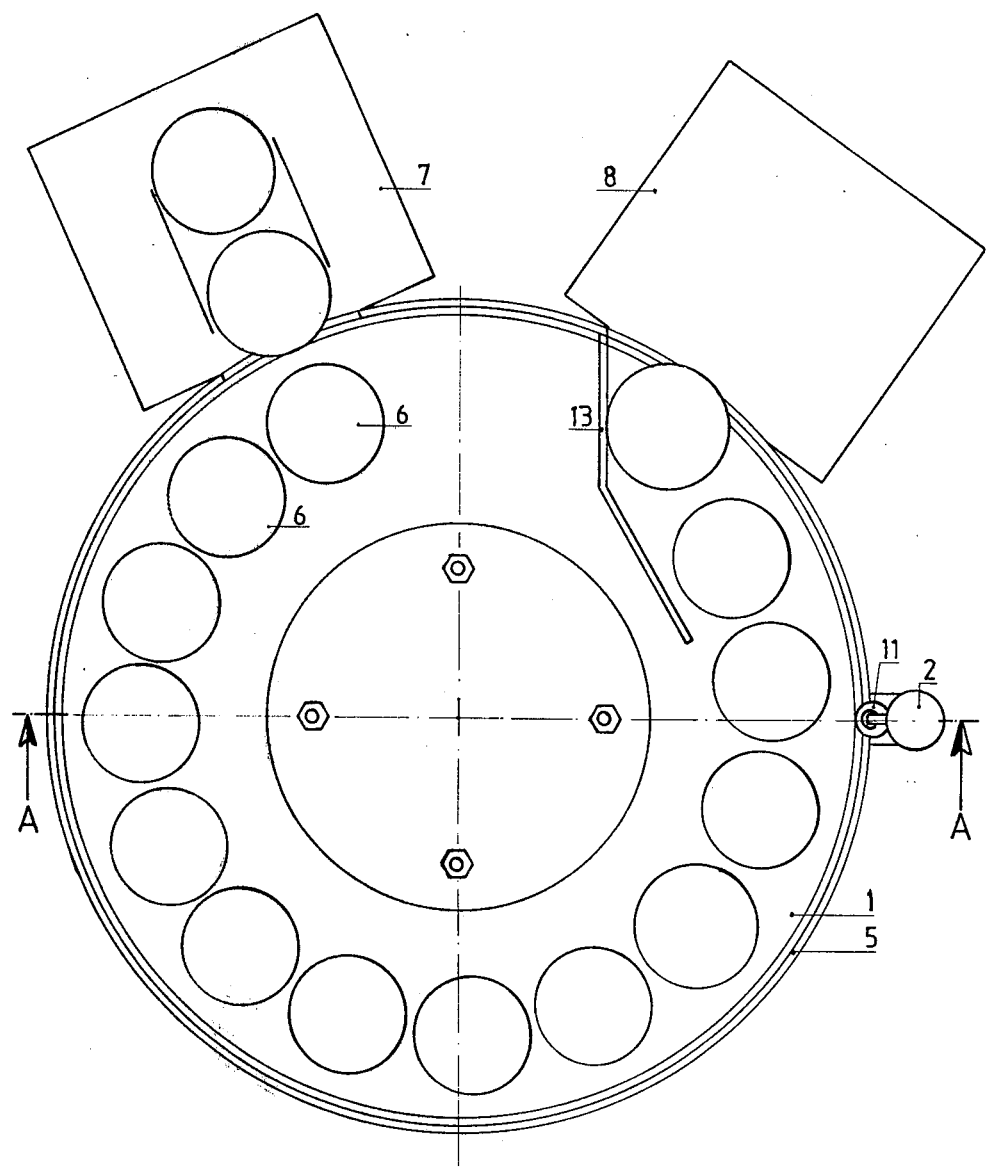
FIG. 1 is a plan view of the device according to the invention.
Figure 2:
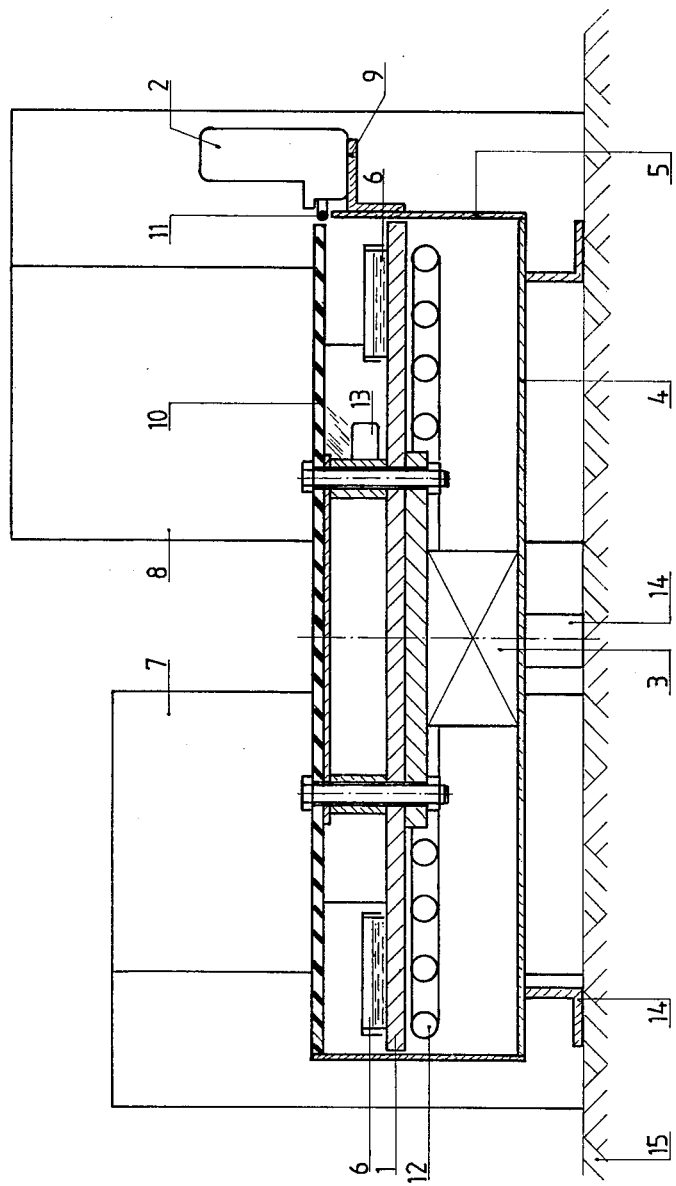
FIG. 2 is a section along line A-A of FIG. 1.

As shown in FIGS. 1 and 2, the device comprises a horizontally rotatable disc 1 made of a preferably highly heat-conducting material, such as aluminum, brass, copper, or similar material. The mass of the disc is such that oscillations, caused by switching on and off of a motor 2 for driving the disc, are entirely suppressed. The disc 1 is supported by a bearing 3 mounted on the bottom of a circular box 4 provided with an upright flange 5 that surrounds the disc 1. The flange 5 is provided with some recesses in order that petri-dishes 6, some of them being indicated in the drawing, may be supplied from a supplier 7 and, after the cooling operation, may be transported to a stacker 8. A further recess is made for a driving means, generally designated 9, driven by the motor 2. Above the disc 1, and mounted thereto, a protecting hood or plate 10 is arranged, which is preferably made of a transparent material such as perspex, so that petri-dishes on the disc are visible. The driving means 9 utilizes flexible driving device, such as a pulley 11 with rubber ring, that is driven by the motor 2, to rotate the protecting plate 10 and the disc 1. The pulley 11 serves to transfer force from the motor to the plate 10 and disc 1. A cooling means 12, consisting of a spiralized tube, is arranged just below the lower surface of the disc 1 and may be passed by a cooling liquid from a cooling source (not illustrated). The cooling temperature is regulated by means of a thermal switch, also arranged below the surface of the disc 1, preferably below the part of the disc between the entering and leaving locations of the petri-dishes, where normally no petri-dishes are positioned. For the transfer of the petri-dishes from the disc 1 to the stacker 8, a guiding strip 13 is arranged just above the disc 1, mounted on the flange 5 of the box 4. The whole device is provided with legs 14, allowing the device to stand on a table 15 or the like, together with other apparatuses.

In the embodiment indicated in the drawing, it is possible to use a signal from the stacker 8, which regulates stacking of the petri-dishes and regulates supply of a petri-dish each time from the supplier, to also operate the driving motor 2 in such a manner that the disc 1 is stopped when a petri-dish is supplied from the supplier 7, and the disc is then rotated until the moment the following petri-dish is to be supplied. The motor 2 can also continuously rotate the disc.

Previously, a specific embodiment of the present invention has been described. It should be appreciated, however, that this embodiment has been described for the purposes of illustration only, without any intention of limiting the scope of the present invention. Rather, it is the intention that the present invention be limited only by the appended claims.

I claim:

1. Device for solidifying a layer of a liquid that solidifies upon cooling, such as agar, contained in a row of petri-dishes or the like, said device comprising:
   a horizontally rotatable disc of heat-conducting material for receiving said dishes,
   means for supplying petri-dishes or the like to said disc,
   means for removing the petri-dishes with solidified liquid from the disc,
   cooling means positioned below the disc for cooling the disc, and
   means for slowly rotating the disc from said means for supplying to said means for removing so that the surface of material in the dishes solidifies in a non-rippled manner.

2. Device according to claim 1, wherein said disc has a relatively large moment of inertia.

3. Device according to claim 1 or 2, characterized in that said means for slowly rotating comprises means for flexibly driving said disc.

4. Device according to claim 3, characterized in that the means for flexibly driving comprises transfer means utilizing an elastic material, such as rubber.

5. Device according to claim 4, characterized in that the driving means further comprises a motor with a slow start and stop.

6. Device according to claim 5, characterized in that the means for flexibly driving said disc comprises a driving means located at the periphery of the disc.

7. Device according to claim 1, characterized in that said means for rotating intermittently rotates said disc so that each petri-dish or the like to be cooled may be pushed onto the disc when the disc is standing still.

8. Device according to claim 1, characterized in that the disc is rotated continuously.

9. Device according to claim 1, characterized in that a protecting hood is provided for the disc and that the disc is driven at the periphery of said hood.

10. Device according to claim 1, characterized in that the rotation speed of the disc is regulated on the basis of the amount of liquid to be dosed in the petri-dishes.

11. A device for solidifying a layer of a liquid that solidifies upon cooling, such as agar, contained in a row of petri-dishes or the like, said device comprising:
    a horizontally rotatable disc of heat-conducting material for receiving said dishes,
    means for supplying petri-dishes or the like to said disc,
    means for removing the petri-dishes with solidified liquid from the disc,
    cooling means positioned below the disc for uniformly cooling the disc, and means for rotating the disc from said means for supplying to said means for removing,
    wherein the device is structured such that the disc is rotated and cooled in such a manner to result in a smooth non-rippled surface for the solidified liquid in the dish.

* * * * *